United States Patent [19]

Galambos et al.

[11] Patent Number: 4,758,666
[45] Date of Patent: Jul. 19, 1988

[54] PROCESS FOR THE PREPARATION OF AN APOVINCAMINOL DERIVATIVE

[75] Inventors: János Galambos; Tibor Keve; Béla Stefko; György Fekete; Béla Zsadon; Anna Kassai née Zieger; Klára Horváth née Otta, all of Budapest, Hungary

[73] Assignee: Richter Gedeon Vegyeszeti Gyar R.T., Budapest, Hungary

[21] Appl. No.: 861,550

[22] Filed: May 9, 1986

[30] Foreign Application Priority Data

May 10, 1985 [HU] Hungary ............... 1758/85

[51] Int. Cl.⁴ ........................... C07D 461/00
[52] U.S. Cl. ........................................ 546/51
[58] Field of Search ........................ 546/51

[56] References Cited

U.S. PATENT DOCUMENTS 4,424,223 1/1984 Keve et al. ............... 514/283

FOREIGN PATENT DOCUMENTS 2094297 9/1982 United Kingdom ......... 514/283

OTHER PUBLICATIONS

English language translation of Ger. Off. 2 832 587, the underlying reference in the Chem. Abstracts (S) reference to Lorincz et al (T).
Najer, et al., Chemical Abstracts, vol. 82:4451p (1975).
Najer, et al., Chemical Abstracts, vol. 84:105884d (1976).
Lorincz, et al., Chemical Abstracts, vol. 91:20863r (1979).
Corvi Mora, Chemical Abstracts, vol. 88:105636g (1978).

*Primary Examiner*—Donald G. Daus
*Assistant Examiner*—Diana G. Rivers
*Attorney, Agent, or Firm*—Herbert Dubno; Jonathan Myers

[57] ABSTRACT

The invention relates to a new process for the preparation of 17,18-dehydro-apovincaminol-trimethoxy-benzoate of the formula (I)

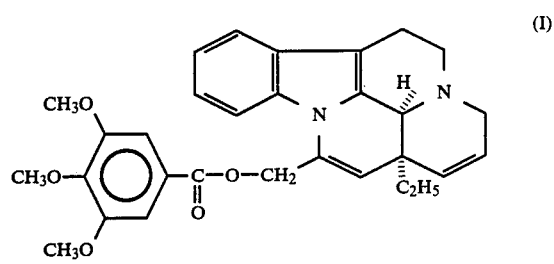

and acid addition salts thereof.

According to the invention compound of the formula (I) is prepared starting from 17,18-dehydrovincamine of the formula (IIa)

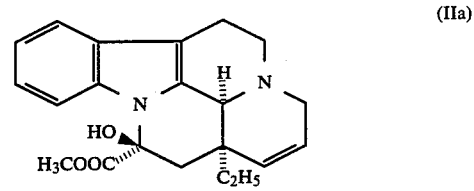

and/or 17,18-dehydro-epivincamine of formula (IIb)

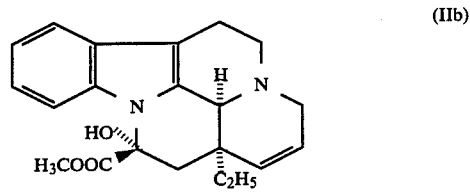

by reducing with a complex metal hydride, acylating the new hydroxy-vincaminol derivative obtained selectively with 3,4,5-trimethoxy-benzoic acid or a derivative thereof capable of acylation, optionally in the presence of a catalyst and/or an acid binding agent, and treating the corresponding acylated hydroxylderivative obtained with formic acid, in the presence of an acid chloride, and, if desired, converting the compound of formula (I) obtained into an acid addition salt thereof.

4 Claims, No Drawings

PROCESS FOR THE PREPARATION OF AN APOVINCAMINOL DERIVATIVE

The invention relates to a new process for the preparation of an apovincaminol derivative. More particularly, the invention concerns a new process for the preparation of 17,18-dehydro-apovincaminol-3',4',5'-trimethoxy-benzoate of the formula (I)

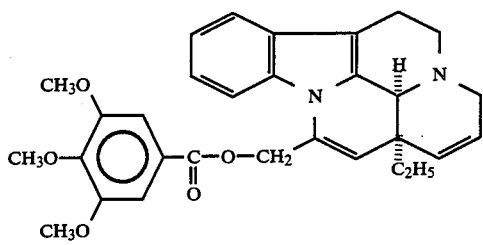

and acid addition salts thereof.

In the formula (I) and in all of the other formulae the broken line indicates that the substituent is in α-position, the arrow indicates that the substituent is in β-position and the wavy line indicates that the stereochemical position of the substituent is not defined.

It is known for example from the British Patent Specification No. 2,094,297 that 17,18-dehydro-apovincaminol-3',4',5'-trimethoxy-benzoate of the formula (I) inhibits phosphodiesterase enzyme activity and is therefore suitable for the treatment of psoriasis. According to the cited British Patent Specification the compound was prepared starting from 17,18-dehydro-vincamine of the formula (IIa)

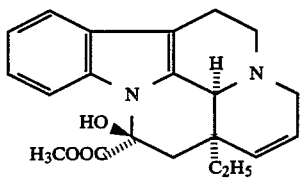

or 17,18-dehydro-epivancamine of the formula (IIb)

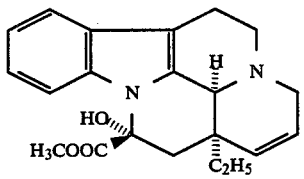

or a mixture thereof. The known starting compounds of the formula (IIa) or (IIb) or a mixture thereof were treated with a suitable dehydrating agent to yield 17,18-dehydro-apovincamine, which was then converted into 17,18-dehydro-apovincaminol by treatment with a selective reducing agent. The product obtained was acylated with 3,4,5-trimethoxy-benzoic acid or a derivative thereof capable of acylation to yield the compound of the formula (I).

According to the Examples dehydration was performed in a chloroformic solution, in the presence of formic acid and acetyl chloride, the reduction was carried out with lithium-aluminium hydride in diethyl ether while the acylation was accomplished with trimethoxy-benzoyl chloride, in a benzene solution.

We have experimentally found that in practice the above process has the following disadvantages:

(1) When preparing 17,18-dehydro-apovincaminc acid according to Example 1 of the British Patent Specification No. 2,094,297 or under other conditions known in the art for the dehydration of analogous compounds, the hydroxyl group of the compounds of the formulae (IIa) and (IIb) can not be completely eliminated and the starting hydroxy-compound contaminates the product obtained by the reaction.

(2) The acylation is performed with a large excess of the acylating agent, which is difficult to eliminate from the reaction mixture. The excess of the acylating agent may separate out together with the product in a crystalline form and accordingly increases the impurity content of the product.

(3) During the multi-step synthesis starting from the compounds of the formulae (IIa) and (IIb) two intermediates are isolated. This multiple isolation decreases the yield of the end product. Since these intermediates are readily crystallizable compounds they may crystallize together with the end product if they are left in the reaction mixture, i.e. will accompany the end product as further impurities. Another drawback of the isolation of the two intermediate compounds is the increase of the manufacturing time due to the time required for drying of the intermediates.

The purpose of the invention is to provide a simple and quick method which is devoid of the above disadvantages.

According to the invention the compound of the formula (I) is prepared starting from the compounds of the formulae (IIa) and/or (IIb) through new intermediates, preferably without isolating the intermediary compounds, with an excellent yield and in a high purity.

Accordingly, the invention relates to a new process for the preparation of 17,18-dehydro-apovincaminol-3',4',5'-trimethoxy-benzoate of the formula (I), which process comprises (a) reacting 17,18-dehydro-vincamine of the formula (IIa)

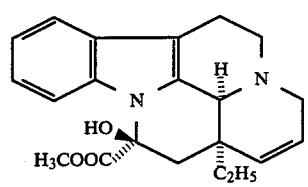

and/or 17,18-dehydro-epivincamine of the formula (IIb)

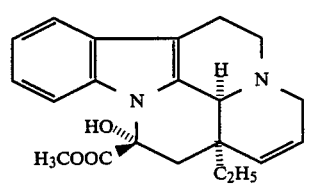

with a complex metal hydride, acylating the vincaminol derivative of the formula (III)

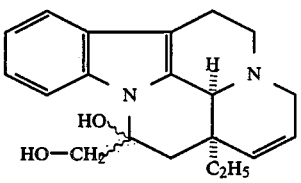

(III)

obtained selectively with 3,4,5-trimethoxy-benzoic acid or a derivative thereof capable of acylation, optionally in the presence of a catalyst and/or an acid binding agent, treating the acylated hydroxyl-derivative of the formula (IV)

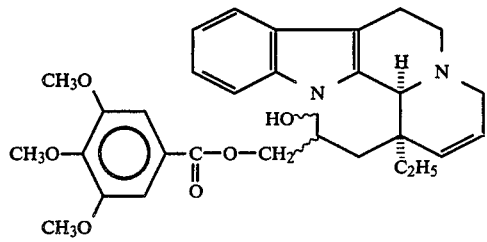

(IV)

obtained with formic acid in the presence of an acid chloride and isolating the product of the formula (I) and if desired, converting same into an acid addition salt thereof; or (b) acylating a vincaminol derivative of the formula (III) selectively with 3,4,5-trimethoxybenzoic acid or a derivative thereof capable of acylation, optionally in the presence of a catalyst and/or an acid binding agent, treating the acylated hydroxyl-derivative of the formula (IV) obtained with formic acid in the presence of an acid chloride, and isolating the product of the formula (I) and if desired, converting same into an acid addition salt thereof; or (c) treating an acylated hydroxyl-derivative of the formula (IV) with formic acid in the presence of an acid chloride, and isolating the product of the formula (I) and if desired, converting same into an acid addition salt thereof.

In the process according to the invention, similarly to the British Patent Specification No. 2,094,297, compounds of the formulae (IIa) or (IIb) or a mixture thereof are used as starting material.

As a complex metal hydride generally alkali metal hydrides, preferably lithium-aluminium hydride are employed. The reduction is carried out in a solvent, preferably in cyclic ethers or toluene or in a mixture thereof. As a derivative of 3,4,5-trimethoxy-benzoic acid capable of acylation the acid as such or a corresponding acid chloride or acid anhydride may be employed. Typical catalysts include 4-dimethylamino-pyridine, 4-pyrrolidino-pyridine and other pyridine derivatives, while as an acid binding agent for example triethyl amine, pyridine or other alkaline substances may be used.

According to a preferred embodiment of the invention compounds of the formulae (IIa) or (IIb) or a mixture thereof are reduced with lithium-aluminium hydride in a mixture of toluene and tetrahydrofuran to yield the new compound of the formula (III). Thereafter, the primary hydroxyl group of the hydroxymethyl group in the above compound is selectively acylated with an equivalent amount of the acylating agent (e.g. trimethoxybenzoyl chloride), in the presence of a catalyst, preferably 4-dimethylamino-pyridine. The selective acylation is based on the different reactivity of the secondary and primary alcohols and yields the new compound of the formula (IV), which is then converted into 17,18-dehydro-apovincaminol-trimethoxy-benzoate of the formula (I) by abstracting one mole of water by means of formic acid and acetyl chloride.

If desired, the product obtained may be converted into an acid addition salt thereof. Preferred representatives of the inorganic acid addition salts are e.g. chlorohydrates, sulfate and phosphate salts. The preferred organic acid addition salts include e.g. the hydrogen tartarate, succinate, citrate and ascorbate salts. The salts are prepared by adding an alcoholic, ethereal or acetone solution of the acid component to the product of formula (I). The preparation of salts is carried out at a pH between 3 and 6.

The main advantage of the process according to the invention is that the intermediates need not be isolated before the subsequent reaction steps, only the excess of the reactants is eliminated by extraction or filtration to avoid decomposition during the heat treatment taking place when the product is isolated. At the end of the synthesis the product can be separated from the poorly crystallizable by-products with a high yield, in an excellent purity.

The process according to the invention is further illustrated by the following Examples which are not intended to limit the scope of the invention in any way.

EXAMPLE 1

(A) 100.0 g of a mixture of 17,18-dehydrovincamine and 17,18-dehydro-epivincamine are suspended in 435.0 g (500 ml) of toluene and the reaction mixture is cooled to 0° C. Thereafter 15.0 g. of lithium-aluminium hydride are added to the reaction mixture, followed by the addition of 88.7 g (100 ml) of absolute tetrahydrofurane in 10 minutes. When the addition is complete, the reaction mixture is heated up to 60° to 70° C. The reaction terminates in 0.5 to 1 hour [the progress of the reaction is monitored by thin layer chromatography (t.l.c.) on silica gel, using a 3:1 mixture of benzene and methanol]. The reaction mixture is then cooled to 0° C. and 50.0 g (50 ml) of water are added in 20 minutes, under vigorous stirring. Thereafter 1320 g (1000 ml) of dichloromethane and 75.0 g of dry sodium sulfate are added to the mixture obtained. The precipitated aluminium hydroxide and the sodium sulfate are filtered off and washed with two 100-ml (132 g) portions of dichloromethane. The dichloromethane solution obtained contains 95% of 17,18-dehydro-vincaminol.

(B) To the solution obtained in Step (A) 1.0 g of dimethylamino-pyridine and 27.2 g (36 ml) of triethyl amine are added, followed by the dropwise addition of a solution of 1 molar equivalent of trimethoxy-benzoyl chloride in 924.0 g (700 ml) of dichloromethane. Addition time: one hour.

The progress of the reaction is monitored by t.l.c. on silica gel, using a 3:1 mixture of benzene and methanol. The reaction is complete in 2.5 hours.

The reaction mixture is then washed with two 1000-ml portions of a 2% aqueous sodium hydroxide solution and subsequently two 1000-ml portions of water and the organic phase is dried over sodium sulfate. The sodium sulfate is filtered off. The dichloromethane solution contains 83.5% of 17,18-dehydro-vincaminol-3',4',5'-trimethoxy-benzoate.

(C) To the solution obtained in Step (B) 183.0 g (150 ml) of dry formic acid and 347 g (250 ml) of acetyl chloride are added at room temperature. After stirring for four hours a further 69.4 g (50 ml) portion of acetyl chloride is added to the reaction mixture.

The progress of the reaction is monitored by t.l.c. (silica gel, 3:1 mixture of benzene and methanol). After termination of the reaction (altogether about 6 hours) 500 ml of water are added to the reaction mixture, whereupon the pH is adjusted to 8 with concentrated ammonium hydroxide under continuous stirring and cooling. The organic phase is separated. The aqueous phase is extracted with 660 g (500 ml) of dichloromethane. The combined organic phase is dried over anhydrous sodium sulfate. Sodium sulfate is filtered off, the filtrate is evaporated in vacuum, at a temperature of at most 60° C., whereupon the solvent is exchanged by dry ethanol during distillation. The final volume is about 150 to 200 ml. The suspension obtained is allowed to stand at 0° to 5° C. for 12 hours. The crystals are filtered off, washed with two 100-ml portions of cold ethanol and dried (under protection from light, at a temperature of at most 50° C.). 114.1 g of 17,18-dehydro-apovincaminol-3',4',5'-trimethoxy-benzoate are obtained.

Yield: 80.3%
Melting point: 142° to 143° C.
$[\alpha]_D = +26.5°$ (c=1, chloroform)
u.v. spectrum (EtOH) $\lambda_{max}$: 261, 303, 314 nm
i.r. spectrum (KBr) $\nu_{max}$ (cm$^{-1}$):
1722 (>C=O)
1650 (>C=C<)
1591 ⎫
1504 ⎭ (Ar skel.)
1215 (Ar—O—C)
1128 (C—O—C)
865 [Ar(1H)]
743 [Ar(4H)]

$^1$H n.m.r. spectrum (CDCl$_3$) δ(ppm):

| | |
|---|---|
| 1.04 (t) | H-21 |
| 1.78 (q) | H-20 |
| 2.45–3.60 (m) | H-5, 6, 19 |
| 3.73 (s) | O—CH$_3$ (3',5') |
| 3.85 (s) | O—CH$_3$ (4') |
| 4.31 (s) | H-3 |
| 5.20 (s) | H-15 |
| 5.34 (d) | H-17 |
| 5.37; 5.48 (d) | O—CH$_2$— |
| 5.53 (m) | H-18 |
| 7.00–7.65 (m) | H-9,10,11,12 |
| 7.21 (s) | H-2',6' |

Physical data of the intermediates:
A. 17,18-Dehydro-vincaminol
u.v. spectrum (EtOH) $\lambda_{max}$ (nm): 230, 282, 290
i.r. spectrum (KBr) $\nu_{max}$ (cm$^{-1}$): 3380 (OH), 1653 (C=C), 1105 [C—O(H)], 1038 [C—O(H)], 741 [Ar(4H)]
$^1$H-n.m.r. spectrum (CDCl$_3$) δ(ppm):

| | |
|---|---|
| 1.01 (t) | H-21 |
| 1.64; 1.91 (m) | H-20 |
| 2.23 (d) | H-15 (ax) |
| 2.42 (d) | H-15(eq) |
| 2.45–3.50 (m) | H-5, 6, 19 |
| 2.75 (br*) | O—H |
| 3.98 (s) | H-3 |
| 5.60 (m) | H-18 |
| 5.72 (d) | H-17 |
| 7.0–7.63 (m) | H-9, 10, 11, 12. |

B. 17,18-dehydro-vincaminol-3',4',5'-trimethoxy-benzoate
U.V. spectrum (EtOH) $\lambda_{max}$ (nm): 273
i.r. spectrum (KBr) $\nu_{max}$ (cm$^{-1}$):
3524 OH
1718 (>C=O)
1653 (>C=C<)
1221 Ar—O—C
1128 C—O—C
1107 C—O(H)
865 Ar (1H)
741 Ar (4H)

$^1$H n.m.r. spectrum (CDCl$_3$) δ(ppm):

| | |
|---|---|
| 1.01 (t) | H-21 |
| 1.6 (br*) | OH |
| 1.65; 1.93 (m) | H-20 |
| 2.31 (d) | H-15(ax) |
| 2.41 (d) | H-15(eq) |
| 2.45–3.5 (m) | H-5, 6, 19 |
| 3.75 (s) | O—CH$_3$ (3',5') |
| 3.85 (s) | O—CH$_3$ (4') |
| 3.99 (s) | H-3 |
| 4.9; 5.0 (d) | O—CH$_2$ |
| 5.62 (m) | H-18 |
| 5.75 (d) | H-17 |
| 7.01 (s) | H-2',6' |
| 7.0–7.7 (m) | H-9,10,11,12 | br*: broad and exchangable by heavy water

EXAMPLE 2

The procedure described in Example 1 is followed except that 17,18-dehydro-apovincaminol-3',4',5'-trimethoxy-benzoate obtained in Step (C) is dissolved in 250 ml. of ethanol and D-tartaric acid is added to the solution until the precipitation of the tartarate salt is complete.

Melting point: 110° to 112° C. (decomp.)
Analysis for C$_{34}$H$_{38}$O$_{11}$N$_2$ (650): calculated: N=4.3%; found: N=4.24%.
u.v. spectrum $\lambda_{max}$ (nm): 209, 251, 304, 315.

We claim:
1. A process for preparing a compound of the Formula

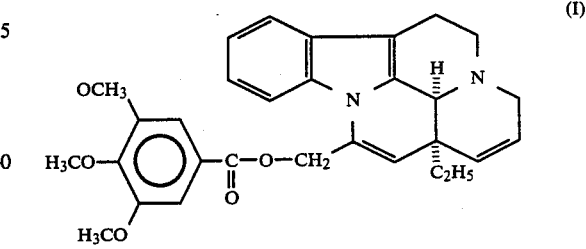

(I)

or a pharmaceutically acceptable acid addition salt thereof, which comprises the steps of:
(a) selectively acylating a compound of the Formula (III)

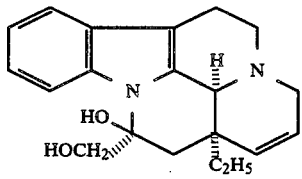

(III)

with an equivalent amount of trimethoxybenzoyl chloride in the presence of dimethylaminopyridine and triethylamine to obtain a compound of the Formula (IV)

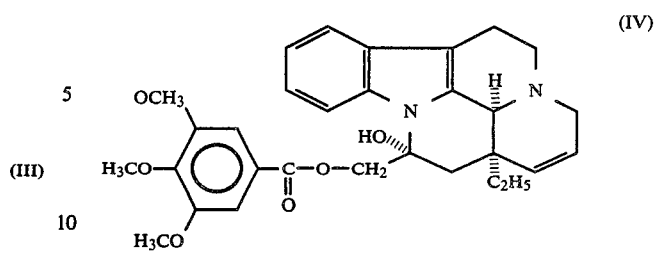

and;

(b) dehydrating the compound of the Formula (IV) with a mixture of formic acid and acetyl chloride to yield the compound of the Formula (I), and in the case where the Formula (I) compound is to be obtained in the form of a pharmaceutically acceptable acid addition salt, converting the compound of the Formula (I) to said pharmaceutically acceptable acid addition salt with a pharmaceutically acceptable acid.

2. The process defined in claim 1, wherein according to step (a), dichloromethane is employed as a solvent.

3. The process defined in claim 1, wherein according to step (b), dichloromethane is employed as the solvent.

4. The process defined in claim 1, wherein according to step (b), the acetyl chloride is added to the reaction mixture in two portions, four hours apart, under stirring.

* * * * *